(12) United States Patent
Aldridge

(10) Patent No.: US 8,465,523 B2
(45) Date of Patent: Jun. 18, 2013

(54) APPARATUS AND SYSTEM FOR VERTEBRAE STABILIZATION AND CURVATURE CORRECTION, AND METHODS OF MAKING AND USING SAME

(76) Inventor: James H. Aldridge, Augusta, MI (US)

( * ) Notice: Subject to any disclaimer, the term of this patent is extended or adjusted under 35 U.S.C. 154(b) by 337 days.

(21) Appl. No.: 13/005,817

(22) Filed: Jan. 13, 2011

(65) Prior Publication Data

US 2011/0152939 A1 Jun. 23, 2011

Related U.S. Application Data

(63) Continuation-in-part of application No. 12/838,116, filed on Jul. 16, 2010, now abandoned.

(60) Provisional application No. 61/288,273, filed on Dec. 19, 2009.

(51) Int. Cl.
*A61B 17/70* (2006.01)

(52) U.S. Cl.
USPC ............................................. 606/246

(58) Field of Classification Search
CPC .................................................. A61B 17/70
USPC ............... 606/246, 264–270, 272, 274, 278, 606/279, 301, 328; 403/359.3, 359.5; 411/346
See application file for complete search history.

(56) References Cited

U.S. PATENT DOCUMENTS

| | | | |
|---|---|---|---|
| 4,048,897 | A | 9/1977 | Price, Jr. |
| 4,826,376 | A | 5/1989 | Aldridge et al. |
| 6,050,766 | A | 4/2000 | Kies et al. |
| 7,060,066 | B2 | 6/2006 | Zhao et al. |
| 7,198,627 | B2 | 4/2007 | Bagga et al. |
| 7,201,753 | B2 | 4/2007 | Schlapfer et al. |
| 2006/0293670 | A1 | 12/2006 | Smisson, III et al. |
| 2007/0016190 | A1 | 1/2007 | Martinez et al. |

*Primary Examiner* — Eduardo C Robert
*Assistant Examiner* — David Comstock
(74) *Attorney, Agent, or Firm* — Weiner & Burt, P.C.; Irving M. Weiner; Pamela S. Burt

(57) ABSTRACT

An apparatus and system useful as a stabilization or correction system for a spinal column. A threaded rod is used that can be straight, rigid, bent or flexible depending on the vertebrae condition to be addressed. The rod may be bent or flexible to achieve varying degrees of lordosis (backward curvature) or kyphosis (forward curvature) before being affixed to the anchoring means and apparatus. The straightness, curvature, bent, or flexibility of rod depends upon the location along the spinal column. Once installed to the vertebrae, the rod provides the proper, desired curvature and stabilization for the spinal column. Sharp edges and corners of the apparatus are eliminated by rounding the edges and corners.

20 Claims, 4 Drawing Sheets

APPARATUS AND SYSTEM FOR VERTEBRAE STABILIZATION AND CURVATURE CORRECTION, AND METHODS OF MAKING AND USING SAME

The present application is continuation-in-part of and claims priority from U.S. patent application Ser. No. 12/838,116 filed Jul. 16, 2010, now abandoned which in turn claims priority from and is based on U.S. Provisional Patent Application 61/288,273 filed Dec. 19, 2009.

BACKGROUND OF THE INVENTION

The present invention relates generally to an apparatus and system for stabilizing and/or correcting the curvature of external members, and methods of making and using same.

More particularly, the present invention relates to an apparatus and system for stabilizing and/or correcting the curvature of vertebrae, and methods of making and using same.

The prior, but not necessarily relevant, art is exemplified by: Price, Jr. U.S. Pat. No. 4,048,897; Kies et al. U.S. Pat. No. 6,050,766; Zhao et al. U.S. Pat. No. 7,060,066; and Martinez et al. United States Patent Application Publication 2007/0016190.

It is a desideratum of the present invention is to avoid the animadversion, disadvantages and deficiencies of conventional devices and techniques, and to provide a novel apparatus and system that eliminates constant, time-consuming, and difficult adjustments.

SUMMARY OF THE INVENTION

The present invention provides an apparatus, comprising: a main central member having rounded edges; a first generally C-shaped lock nut member having rounded edges, a partially cylindrical knurled outer surface, and an internally axial bore portion; the first generally C-shaped lock nut member being connected to a first end of the main central member; first connection means for axially connecting the first generally C-shaped lock nut member and the main central member to permit free relative rotation and limited axial displacement therebetween while preventing total separation thereof; a second generally C-shaped lock nut member having rounded edges, a partially cylindrical knurled outer surface, and an internally axial bore portion; the second generally C-shaped lock nut member being connected to a second end of the main central member; second connection means for axially connecting the second generally C-shaped lock nut member and the main central member to permit free relative rotation and limited axial displacement therebetween while preventing total separation thereof; an anchoring device extending from the main central member; and the anchoring device permitting anchoring the apparatus to an external member.

The present invention also provides a system, comprising, in combination: a first apparatus having: a first main central member having rounded edges; a first generally C-shaped lock nut member having rounded edges, a partially cylindrical knurled outer surface, and an internally axial bore portion; the first generally C-shaped lock nut member being connected to a first end of the first main central member; first connection means for axially connecting the first generally C-shaped lock nut member and the first main central member to permit free relative rotation and limited axial displacement therebetween while preventing total separation thereof; a second generally C-shaped lock nut member having rounded edges, a partially cylindrical knurled outer surface, and an internally axial bore portion; the second generally C-shaped lock nut member being connected to a second end of the first main central member; second connection means for axially connecting the second lock nut member and the first main central member to permit free relative rotation and limited axial displacement therebetween while preventing total separation thereof; a first anchoring device extending from the first main central member; and the first anchoring device permitting anchoring the first apparatus to a first external member; a second apparatus having: a second main central member having rounded edges; a third generally C-shaped lock nut member having rounded edges, a partially cylindrical knurled outer surface, and an internally axial bore portion; the third generally C-shaped lock nut member being connected to a first end of the second main central member; third connection means for axially connecting the third lock nut member and the second main central member to permit free relative rotation and limited axial displacement therebetween while preventing total separation thereof; a fourth generally C-shaped lock nut member having rounded edges, a partially cylindrical knurled outer surface, and an internally axial bore portion; the fourth generally C-shaped lock nut member being connected to a second end of the second main central member; fourth connection means for axially connecting the third generally C-shaped lock nut member and the second main central member to permit free relative rotation and limited axial displacement therebetween while preventing total separation thereof; a second anchoring device extending from the second main central member; and the second anchoring device permitting anchoring the second apparatus to a second external member; whereby the first and second external members are constrained in a predetermined position and orientation relative to one another.

An object of the present invention is to provide an apparatus and system as described hereinabove which is particularly useful as a stabilization and/or correction system for a spinal column and/or portions thereof.

Another object of the present invention is to provide an apparatus as described hereinabove in the form of a 3-part slip-on locking device.

Another object of the present invention is to provide an apparatus and system as described hereinabove wherein the anchoring device is rotationally connected to the main central member.

Another object of the present invention is to provide an apparatus and system as described hereinabove wherein the main central member and the first and second generally C-shaped internally-threaded lock nuts are shaped and dimensioned to permit passage therethrough of an external threaded rod member.

Another object of the present invention is to provide an apparatus and system as described hereinabove wherein the first and second generally C-shaped internally-threaded lock nuts and the first and second connection means are shaped and dimensioned to permit passage therethrough of an external threaded rod member, and to permit selective, adjustable and releasable attachment of the apparatus to the external threaded rod member.

Another object of the present invention is to provide an apparatus and system as described hereinabove wherein the anchoring device is provided with means to threadedly affix the anchoring device to the external member.

Other objects, advantages, and features of the present invention will become apparent to those persons skilled in this particular area of technology and to other persons after having been exposed to the present patent application.

DETAILED DESCRIPTION OF THE INVENTION

Figure 1:
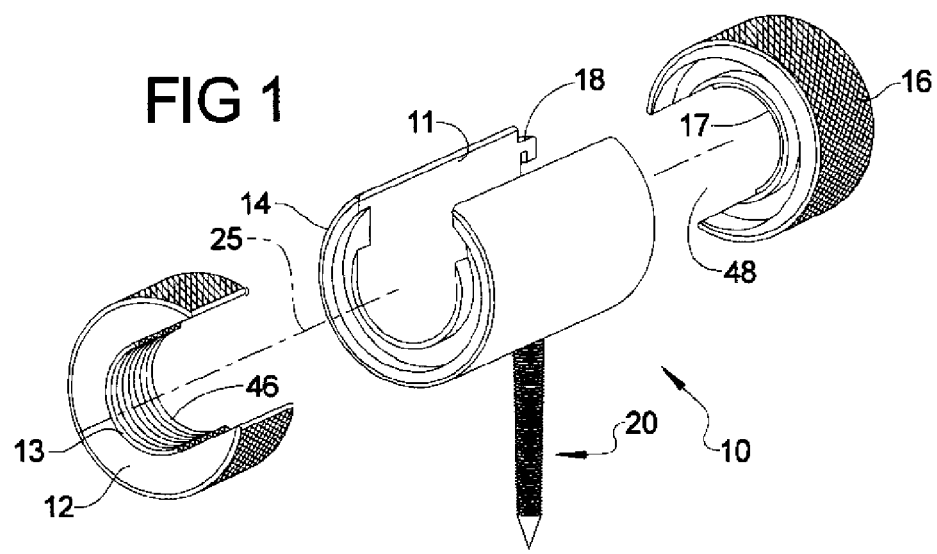
FIG. 1 is a perspective view of a preferred embodiment of the apparatus of the present invention.

With reference to the drawings, there is illustrated an apparatus 10 including a main central member or saddle 11 having rounded edges, and a first generally C-shaped internally-threaded lock nut member 12 having rounded edges, a partially cylindrical knurled outer surface, and an internally axial bore portion 13.

The first or male generally C-shaped internally-threaded lock nut member 12 is connected to a first or female end 14 of the main central member 11.

There is provided first connection means 15 for axially connecting the first generally C-shaped internally-threaded lock nut member 12 and the main central member 11 to permit free relative rotation and limited axial displacement therebetween while preventing total separation thereof.

There is also provided a second generally C-shaped internally-threaded lock nut member 16 having rounded edges, a partially cylindrical knurled outer surface, and an internally axial bore portion 17.

The second or female generally C-shaped internally-threaded lock nut member 16 is connected to a second or male end 18 of the main central member 11.

There is provided second connection means 19 for axially connecting the second generally C-shaped internally-threaded lock nut member 16 and the main central member 11 to permit free relative rotation and limited axial displacement therebetween while preventing total separation thereof.

There is provided a first anchoring device 20 extending from the main central member 11.

The anchoring device 20 permits anchoring the apparatus 10 to a first external member 26, such as a first portion 21 of a vertebrae 22.

The internally-threaded lock nut members 12 and 16 are the male and female members, respectively, of the internally-threaded lock nut arrangement described in detail in Aldridge et al. U.S. Pat. No. 4,826,376, the entire contents of which are incorporated herein by reference thereto.

Figure 4:
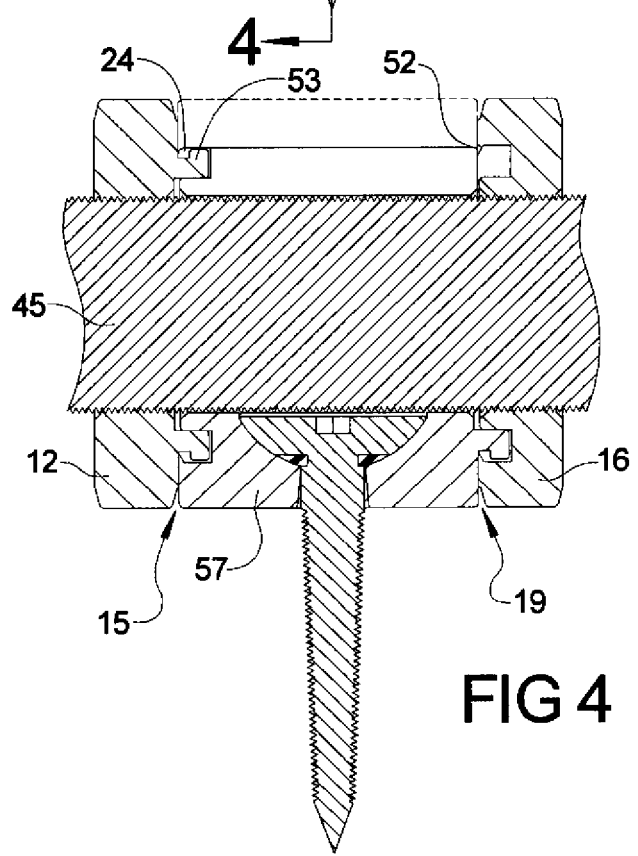
FIG. 4 is a sectional view taken along the line 4-4 in FIG. 3.

With reference to FIGS. 1 and 4, the internally-threaded lock nut members 12 and 16 may individually or together be pressed into the saddle 11 to achieve an interlocking nose 52 and rib 53 arrangement whereby internally-threaded lock nut members 12 and 16 and saddle 11 can freely rotate relative to one another, and are axially affixed to one another to allow limited axial movement, while preventing the complete separation thereof.

The male internally-threaded lock nut member 12 is pressed into the female end 14 of saddle 11 thereby causing the nose 52 of member 12 to deform into the undercut 24 of end 14. Pressing may be achieved using a press mechanism, such as an arbor press or the like.

This causes the member 12 and saddle 11 to be securely axially retained to one another, yet free to rotate relatively to one another about common axis 25.

Figure 2:
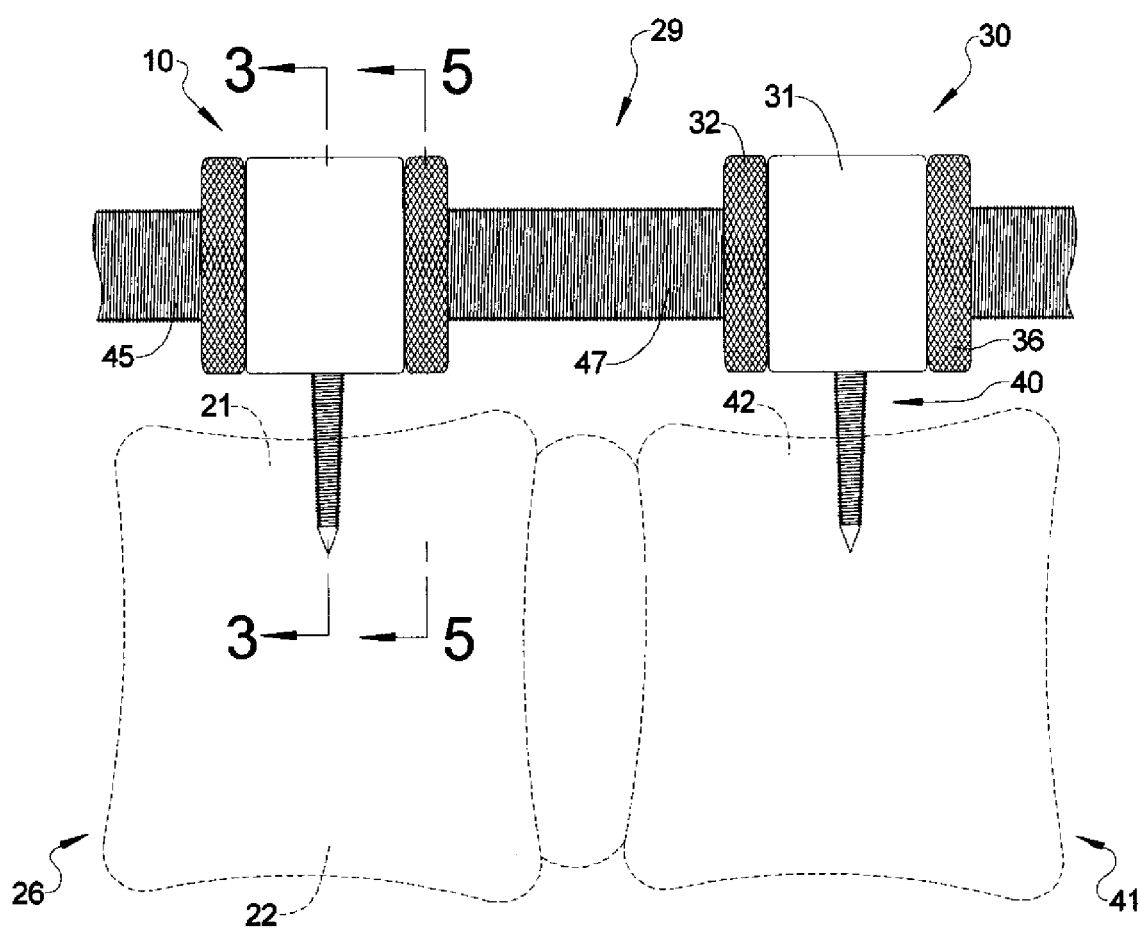
FIG. 2 is an elevational view of a preferred embodiment of the system of the present invention.

With reference to FIG. 2, the system 29 of the invention is illustrated.

System 29 includes the first apparatus 10 and a similar second apparatus 30.

Apparatus 10 has the first anchoring device 20 extending from saddle 11. Device 20 permits anchoring apparatus 10 to the first external member 26, such as the first portion 21 of vertebrae 22.

Apparatus 30 has a second main central member or saddle 31 having rounded edges.

A third generally C-shaped internally-threaded lock nut member 32 has rounded edges, a partially cylindrical knurled outer surface, and an internally axial bore portion.

Member 32 is connected to a first or female end of saddle 31.

Third connection means similar to connection means 15 axially connects member 32 and saddle 31 to permit free relative rotation and limited axial displacement therebetween while preventing total separation thereof.

A fourth generally C-shaped internally-threaded lock nut member 36 has rounded edges, a partially cylindrical knurled outer surface, and an internally axial bore portion.

Member 36 is connected to a second or male end of saddle 31.

Fourth connection means similar to connection means 19 axially connects member 36 and saddle 31 to permit free relative rotation and limited axial displacement therebetween while preventing total separation thereof.

The internally-threaded lock nut members 32 and 36 may be the male and female members, respectively, (or vice versa) of the internally-threaded lock nut arrangements described in detail in Aldridge et al. U.S. Pat. No. 4,826,376, the entire contents of which are incorporated herein by reference thereto.

The male internally-threaded lock nut member 32 is pressed into the female end of saddle 31 thereby causing the nose 52 of member 32 to deform into the undercut 24 of the female end of saddle 31. Pressing may be achieved using a press mechanism, such as an arbor press or the like.

This causes the member 32 and saddle 31 to be securely axially retained to one another, yet free to rotate relatively to one another about the common axis 25.

A second anchoring device 40 extends from saddle 31. Device 40 permits anchoring the second apparatus 30 to a second external member 41, such as a second portion 42 of vertebrae 22.

The system 29 constrains the first and second external members 26 and 41 in a desired predetermined position and orientation relative to one another.

The saddles 11 and 31 and the internally-threaded lock nuts 12, 16, 32 and 36 are shaped and dimensioned to permit passage therethrough of an external threaded rod member 45.

The internally-threaded lock nuts 12, 16, 32 and 36 have internal threads 46 in their respective bore portions to threadedly engage with the thread 47 of rod 45.

Saddles 11 and 31 do not have any threads whatsoever.

Figure 3:
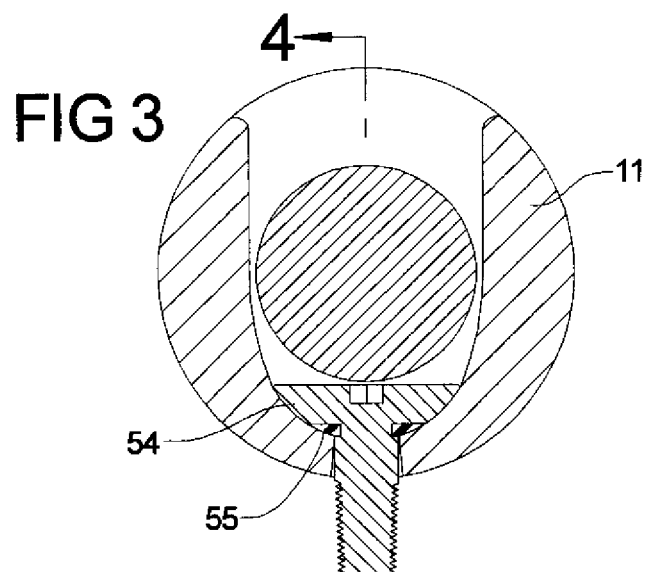
FIG. 3 is a sectional view taken along the line 3-3 in FIG. 2.
Figure 5:
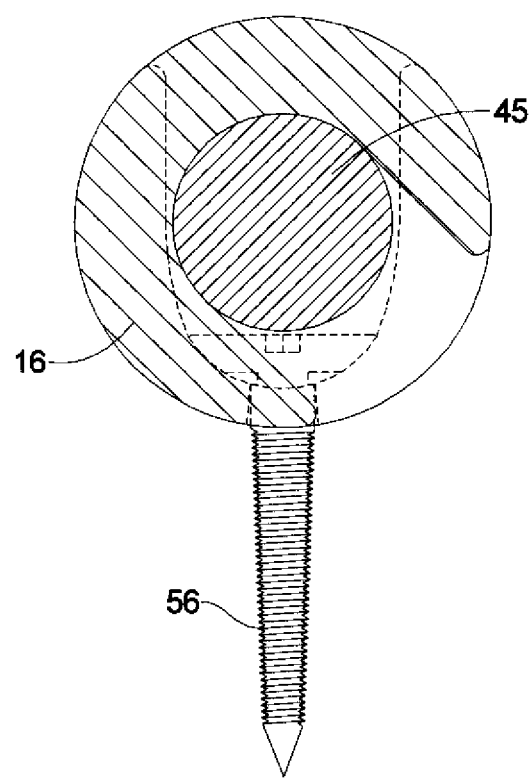
FIG. 5 is a sectional view taken along the line 5-5 in FIG. 2.
Figure 6:
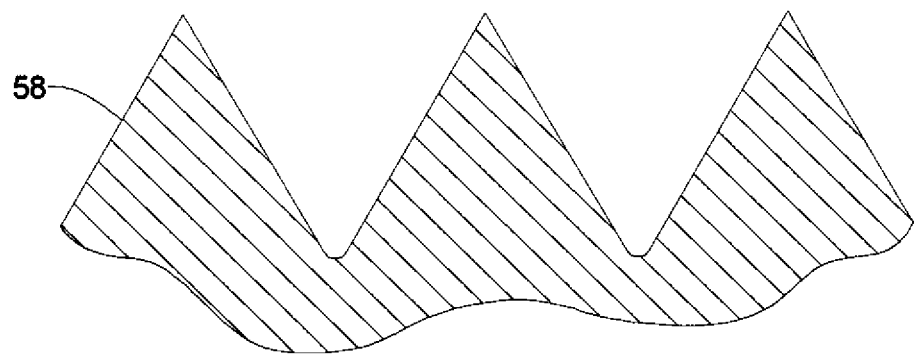
FIG. 6 is a profile of the thread of the anchoring screw.
Figure 7:
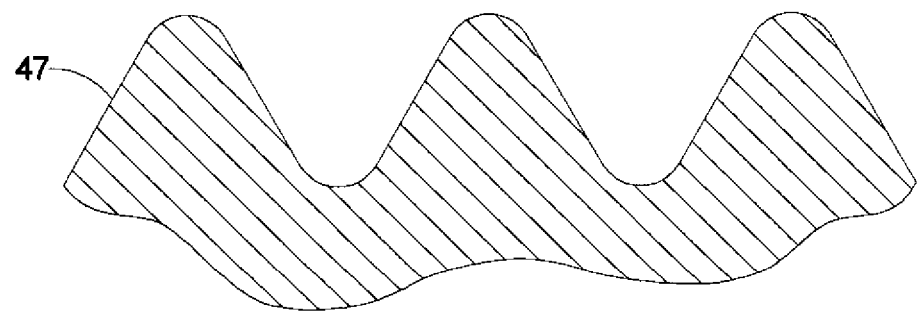
FIG. 7 is a profile of the thread of the rod.

As best seen in FIGS. 3 and 5, rod 45 does not contact saddle 11 or 31. There is a predetermined clearance between the saddle and the rod 45.

The internally-threaded lock nuts 12, 16, 32 and 36 and the connection means 15, 19, 35 and 39 are shaped and dimensioned to permit passage therethrough of threaded rod member 45, and to permit selective and releasable attachment of the apparatuses 10 and 30 to the rod member 45.

Each internally-threaded lock nut 12, 16, 32 and 36 has a slot 48.

In use, each slot 48 is positioned so that the mouth of the slot 48 is directly adjacent the rod 45 at the desired point of use, whereupon the internally-threaded lock nuts 12, 16, 32 and 36 are moved transversely on rod 45 so that the threads 46 and 47 engage. Thereafter, the internally-threaded lock nuts are rotated through a fraction of a revolution to a locked position. Removal is effected by reversing the above-described sequence.

The apparatuses 10 and 30 can be easily positioned anywhere along the length of rod 45.

The rod 45 can easily be removed from the apparatuses 10 and/or 30 or from system 29 for replacement or adjustment.

With reference to FIGS. 3, 4 and 5, the anchoring means 20 or 40 includes an enlarged top portion 54, an O-ring 55, and an elongated threaded member 56. The anchoring means 20 or 40 is rotatably supported in the lower portion 57 of its associated saddle 11 or 31, respectively.

There is also a predetermined clearance between the rod 45 and the uppermost surface of the enlarged top portion 54 of the anchoring means 20 or 40.

The elongated threaded anchoring member 36 is provided with a thread 58, and is used to be selectively and removably threadedly affixed to the external member 26 or 41, such as vertebrae portion 21 or 42, respectively.

The O-ring 55 absorbs shocks, provides adjustability, and minimizes the possibility any breakage to other components of the apparatuses 10 or 30 and system 29. Preferably, the O-ring 55 is fabricated from a resilient and/or elastic material.

The internally-threaded lock nuts 12, 16, 32 and 36 hold the saddle 11 or 31, respectively, on the rod 45 in place.

The threads 46, 47 and 58 are provided with radius roots to increase their strength and tensile strength.

The apparatuses 10 and 30 and system 29 are particularly useful as a stabilization and/or correction system for a spinal column and/or portions thereof.

The rod 45 can be straight and rigid, or bent, or somewhat flexible depending on the vertebrae condition to be addressed.

For example, the rod 45 may be bent or somewhat flexible to achieve varying degrees of lordosis (backward curvature) or kyphosis (forward curvature) prior to being affixed to the anchoring means and associated apparatus.

Also, the straightness, curvature, bent, and/or flexibility of rod 45 also depends upon the location along the spinal column, i.e., the cervical region may have a kyphotic curve, while the lumbar region may have a lordotic curve. Once installed to the vertebrae, the rod 45 provides the proper, desired curvature and/or stabilization for the spinal column.

Because the apparatus 10 and 30 and system 29 may be installed in a patient, the sharp edges and corners of the apparatus are eliminated by rounding all edges and corners.

Alternatively, internally-threaded lock nuts 12 and 32 can be female members; saddle end 14 can be a complementary male member; internally-threaded lock nuts 16 and 36 can be male members; and saddle end 18 can be a complementary female member.

There have been described hereinabove only some of the many possible embodiments of the present invention which can be practiced in many different ways.

Many changes, modifications, variations, and other uses and applications will become apparent to those persons skilled in this particular area of technology and to others after having been exposed to the present patent application.

Any and all such changes, modifications, variations and other uses and applications which do not depart from the spirit and scope of the present invention are therefore covered by and embraced within the patent claims set forth hereinbelow.

The invention claimed is:

1. An apparatus, comprising:
a main central member having rounded edges;
a first generally C-shaped lock nut member having rounded edges, a partially cylindrical knurled outer surface, and an internally axial bore portion;
the first generally C-shaped lock nut member being connected to a first end of the main central member;
first connection means for axially connecting the first generally C-shaped lock nut member and the main central member to permit free relative rotation and limited axial displacement therebetween while preventing total separation thereof;
a second generally C-shaped lock nut member having rounded edges, a partially cylindrical knurled outer surface, and an internally axial bore portion;
the second generally C-shaped lock nut member being connected to a second end of the main central member;
second connection means for axially connecting the second generally C-shaped lock nut member and the main central member to permit free relative rotation and limited axial displacement therebetween while preventing total separation thereof;
an anchoring device extending from the main central member; and
the anchoring device permitting anchoring the apparatus to an external member.

2. The apparatus of claim 1 wherein the anchoring device is rotationally connected to the main central member.

3. The apparatus of claim 2 wherein the anchoring device is provided with means to threadedly affix the anchoring device to the external member.

4. The apparatus of claim 2 wherein the main central member and the first and second generally C-shaped lock nuts are shaped and dimensioned to permit passage therethrough of an external threaded rod member.

5. The apparatus of claim 2 wherein the first and second generally C-shaped lock nuts and the first and second connection means are shaped and dimensioned to permit passage therethrough of an external threaded rod member, and to permit selective and releasable attachment of the apparatus to the external threaded rod member.

6. The apparatus of claim 1 wherein the anchoring device is provided with means to threadedly affix the anchoring device to the external member.

7. The apparatus of claim 6 wherein the main central member and the first and second generally C-shaped lock nuts are shaped and dimensioned to permit passage therethrough of an external threaded rod member.

8. The apparatus of claim 6 wherein the first and second generally C-shaped lock nuts and the first and second connection means are shaped and dimensioned to permit passage therethrough of an external threaded rod member, and to permit selective and releasable attachment of the apparatus to the external threaded rod member.

9. The apparatus of claim 1 wherein the main central member and the first and second generally C-shaped lock nuts are shaped and dimensioned to permit passage therethrough of an external threaded rod member.

10. The apparatus of claim 1 wherein the first and second generally C-shaped lock nuts and the first and second connection means are shaped and dimensioned to permit passage therethrough of an external threaded rod member, and to permit selective and releasable attachment of the apparatus to the external threaded rod member.

11. A system, comprising, in combination:
a first apparatus having:
a first main central member having rounded edges;

a first generally C-shaped lock nut member having rounded edges, a partially cylindrical knurled outer surface, and an internally axial bore portion;

the first generally C-shaped lock nut member being connected to a first end of the first main central member;

first connection means for axially connecting the first generally C-shaped lock nut member and the first main central member to permit free relative rotation and limited axial displacement therebetween while preventing total separation thereof;

a second generally C-shaped lock nut member having rounded edges, a partially cylindrical knurled outer surface, and an internally axial bore portion;

the second generally C-shaped lock nut member being connected to a second end of the first main central member;

second connection means for axially connecting the second lock nut member and the first main central member to permit free relative rotation and limited axial displacement therebetween while preventing total separation thereof;

a first anchoring device extending from the first main central member; and the first anchoring device permitting anchoring the first apparatus to a first external member;

a second apparatus having:

a second main central member having rounded edges;

a third generally C-shaped lock nut member having rounded edges, a partially cylindrical knurled outer surface, and an internally axial bore portion;

the third generally C-shaped lock nut member being connected to a first end of the second main central member;

third connection means for axially connecting the third lock nut member and the second main central member to permit free relative rotation and limited axial displacement therebetween while preventing total separation thereof;

a fourth generally C-shaped lock nut member having rounded edges, a partially cylindrical knurled outer surface, and an internally axial bore portion;

the fourth generally C-shaped lock nut member being connected to a second end of the second main central member;

fourth connection means for axially connecting the third generally C-shaped lock nut member and the second main central member to permit free relative rotation and limited axial displacement therebetween while preventing total separation thereof;

a second anchoring device extending from the second main central member; and the second anchoring device permitting anchoring the second apparatus to a second external member;

whereby the first and second external members are constrained in a predetermined position and orientation relative to one another.

12. The system of claim 11 wherein each said anchoring device is rotationally connected to its associated main central member.

13. The system of claim 12 wherein each said anchoring device is provided with means to threadedly affix the anchoring device to the external member.

14. The system of claim 12 wherein the main central members and the generally C-shaped lock nuts are shaped and dimensioned to permit passage therethrough of an external threaded rod member.

15. The system of claim 12 wherein the generally C-shaped lock nuts and the connection means are shaped and dimensioned to permit passage therethrough of the external threaded rod member, and to permit selective and releasable attachment of the apparatuses to the external threaded rod member.

16. The system of claim 11 wherein each said anchoring device is provided with means to threadedly affix the anchoring device to the external member.

17. The system of claim 16 wherein the main central members and the generally C-shaped lock nuts are shaped and dimensioned to permit passage therethrough of an external threaded rod member.

18. The system of claim 16 wherein the generally C-shaped lock nuts and the connection means are shaped and dimensioned to permit passage therethrough of the external threaded rod member, and to permit selective and releasable attachment of the apparatuses to the external threaded rod member.

19. The system of claim 11 wherein the main central members and the generally C-shaped lock nuts are shaped and dimensioned to permit passage therethrough of an external threaded rod member.

20. The system of claim 11 wherein the generally C-shaped lock nuts and the connection means are shaped and dimensioned to permit passage therethrough of the external threaded rod member, and to permit selective and releasable attachment of the apparatuses to the external threaded rod member.

* * * * *